United States Patent
Nielsen et al.

[11] Patent Number: 5,961,496
[45] Date of Patent: Oct. 5, 1999

[54] SYRINGE WITH TILTABLE NUT FOR QUICK PISTON DISENGAGEMENT

[75] Inventors: Preben Broskov Nielsen, Gilleleje; Henrik Andersen, Værløse, both of Denmark

[73] Assignee: Novo Nordisk A/S, Bagsvaerd, Denmark

[21] Appl. No.: 09/094,311

[22] Filed: Jun. 9, 1998

Related U.S. Application Data

[60] Provisional application No. 60/090,993, Jun. 18, 1997, and provisional application No. 60/054,858, Aug. 6, 1997.

[30] Foreign Application Priority Data

Jun. 17, 1997 [DK] Denmark ................ 0706/97
Jul. 9, 1997 [DK] Denmark ................ 0830/97

[51] Int. Cl.$^6$ ........................... A61M 5/00
[52] U.S. Cl. ........................... 604/209; 604/211
[58] Field of Search ........... 604/207–211, 232, 604/186, 224, 228, 181, 225, 220; 411/433, 437, 950; 222/391

[56] References Cited

U.S. PATENT DOCUMENTS

| | | | |
|---|---|---|---|
| 938,544 | 11/1909 | Ball | 604/211 |
| 3,237,660 | 3/1966 | Hill | 604/211 |
| 3,353,718 | 11/1967 | McLay | 604/211 |
| 3,517,668 | 6/1970 | Brickson | 222/390 |
| 3,878,757 | 4/1975 | Puklus, Jr. | |
| 4,244,366 | 1/1981 | Raines | 604/211 |
| 4,457,712 | 7/1984 | Dragan | 222/391 |
| 5,098,382 | 3/1992 | Haber et al. | 604/232 |
| 5,318,544 | 6/1994 | Drypen et al. | 604/210 |
| 5,336,183 | 8/1994 | Greelis et al. | 604/121 |
| 5,454,793 | 10/1995 | Levander et al. | 604/235 |
| 5,507,727 | 4/1996 | Crainich | 604/97 |
| 5,558,481 | 9/1996 | Park | 411/433 |

FOREIGN PATENT DOCUMENTS 2613789 10/1988 France .
501 676 7/1993 Sweden .

*Primary Examiner*—Wynn Wood Coggins
*Assistant Examiner*—Sharon Finkel
*Attorney, Agent, or Firm*—Steven T. Zelson, Esq.

[57] ABSTRACT

In a syringe dosing mechanism a threaded spindle (1) and a nut (3) cooperates so that relative rotation thereof moves the nut (3) along the spindle (1). The nut (3) has two intersecting bores (12, 15). The first bore (15) has an inner thread (7) matching the outer thread (2) of the spindle (1) and the second bore (12) is smooth and fits slidingly over the spindle (1). The nut (3) is tiltable between a first and a second position. In the first position the threaded bore (15) is coaxial with the spindle (1) and in the second position the smooth bore (12) is coaxial with the spindle (1). The nut (3) is at a first side hinged to a piston rod (6) so that exertion of a force by the nut (3) on the piston rod (6) in a direction (10) by which an injection is performed will tilt said nut (3) into its first position. A piston withdrawal member acts at a second side of said nut diametrically opposite said first side so that the nut (3) is tilted to its second position when the withdrawal member applies a force (13) to said nut (3).

5 Claims, 2 Drawing Sheets

5,961,496

SYRINGE WITH TILTABLE NUT FOR QUICK PISTON DISENGAGEMENT

This application claims priority under 35 U.S.C. 119 of Danish application Ser. Nos. 0706/97 filed on Jun. 17, 1997 and 0830/97 filed on Jul. 9, 1997, and of U.S. provisional application Ser. Nos. 60/050,993, filed on Jun. 9, 1997 and 60/054,858 filed on Aug. 6, 1997, the contents of which are fully incorporated herein by reference.

BACKGROUND OF THE INVENTION

1. Field of the Invention

The invention relates to syringes for dosed injection of a medicine from an exchangeable cartridge of the kind having a piston which is forced into a tubular cartridge to press out a dose of medicine corresponding to the movement of the piston, the syringe having a housing comprising a cartridge holder and a dosing mechanism by which a dose is set and subsequently injected by successively advancing a piston rod to press the piston into the cartridge, said dosing mechanism comprising a threaded spindle and a nut member cooperating with the spindle so that by setting of a dose relative rotation of the spindle and the nut member will move the nut member along the spindle, the position of the nut member on the spindle defining how far the piston rod is advanced during the injection. The spindle may be formed by the piston rod which may be provided with an outer thread.

2. Description of the Related Art

In known syrgines of such type, when the cartridge is empty said piston rod projects into the cartridge in almost the total length thereof. To change the cartridge the piston rod must first be drawn out of the empty cartridge, and thereafter it must be brought back to its initial position in the dose setting part. The last operation is made possible by locks getting unlocked when the empty cartridge is removed from the syringe, where after the piston rod may be pushed or screwed back to its initial position.

The release of said locking may be obtained either by bringing the inner thread of the nut member out of engagement with the spindle or by allowing a free relative rotation of the nut member and the spindle. When the locking is released the nut member, which have during the injections performed been moved to a position on the spindle corresponding to a fully advanced piston rod, may be moved along the spindle back to its position corresponding to a totally retracted piston rod.

By the free rotation of the nut member relative to the spindle the nut may be screwed back to its initial position corresponding to a fully retracted piston rod. However, the nut has to be rotated about 75 turns and this screwing may demand some handiness. This problem may be overcome by using threads with a high pitch and low friction which allows the spindle to rotate by itself when the nut is pressed in the axial direction of said spindle. Another solution is to use a nut member comprising at least two parts which may be pulled apart so that their threads are drawn out of engagement with the thread of the spindle when the nut is going to be returned to its initial position. However, this solution may cause problems when the parts are brought together again to engage the thread of the spindle as it may be difficult to obtain the correct synchronization between the position of the nut member on the spindle and the scale indicating the dose set. Further, the engagement between the threads is dependent on tolerances which may cause wear which makes the settings inaccurate.

BRIEF SUMMARY OF THE INVENTION

It is an object of the invention to provide a nut providing a good engagement with the spindle and the thread of which may easily be brought out of engagement with the thread of the spindle without involving parts which must be moved in relation to each other.

This is obtained by a syringe as described in the opening of this application and in FIG. 1 using a nut which has two intersecting bores forming an angle with each other and of which a first bore has an inner thread matching the outer thread of the spindle and a second bore is smooth and fits slidingly over the thread of the spindle, the nut member being mounted to the piston rod tiltable between a first and a second position so that in the first position the threaded bore is coaxial with the spindle during dose setting and injection and in the second position to which the nut is tilted when acted upon to withdraw the piston rod and move said nut member along the spindle the smooth bore is coaxial with the spindle.

During normal use of the injection device the nut is held with its first bore coaxial with the spindle with the threaded parts of this first bore engaging the outer thread of the spindle. This way the nut may be moved along the spindle when said spindle and the nut are rotated relative to each other. When it is requested to move the nut along the spindle without performing said relative rotation the nut is tilted on the spindle to bring it into a second angular position relative to the spindle in which angular position the second bore is coaxial with the spindle. In this angular position the nut may be displaced along the spindle with the smooth surface of the second bore sliding over the tops of the threads of the spindle. When the nut has been moved to a wanted position along the spindle, the nut is tilted back to its first angular position with the first bore coaxial with the spindle and the threaded parts of this first bore engaging the threads of the spindle.

BRIEF DESCRIPTION OF THE SEVERAL VIEWS OF THE DRAWINGS

In the following the invention is explained in further details with references to the drawing, wherein.

DETAILED DESCRIPTION OF THE INVENTION

Figure 1:
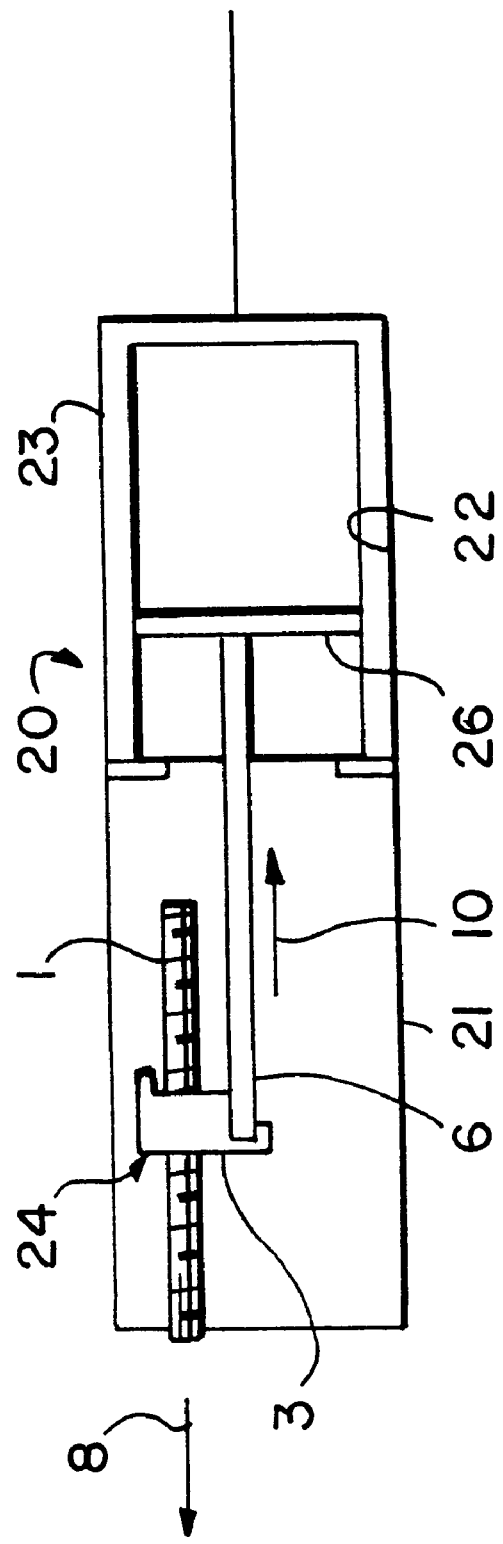
FIG. 1 is a schematic view of a 3 syringe according to the invention, FIG. 2 schematically shows a threaded spindle connected to a piston rod through a tiltable nut with a threaded and a smooth bore, the nut being in a first position with the thread of the bore engaging the thread of the spindle, and FIG. 3 the spindle, nut and piston rod in FIG. 1 only with the nut tilted to a second position so that the spindle runs through the smooth walled bore.

FIG. 1 shows a syringe 20 having a housing 21 including a cartridge holder 22 for holding a cartridge 23 containing a medicine. The housing also includes a dosing mechanism, indicated generally by number 24, comprising a rotatable spindle 1 and a nut 3, which are described in greater detail below. Finally, the syringe includes a piston rod 6 which extends between the nut 3 and a piston 26 within the cartridge 23.

Figure 2:
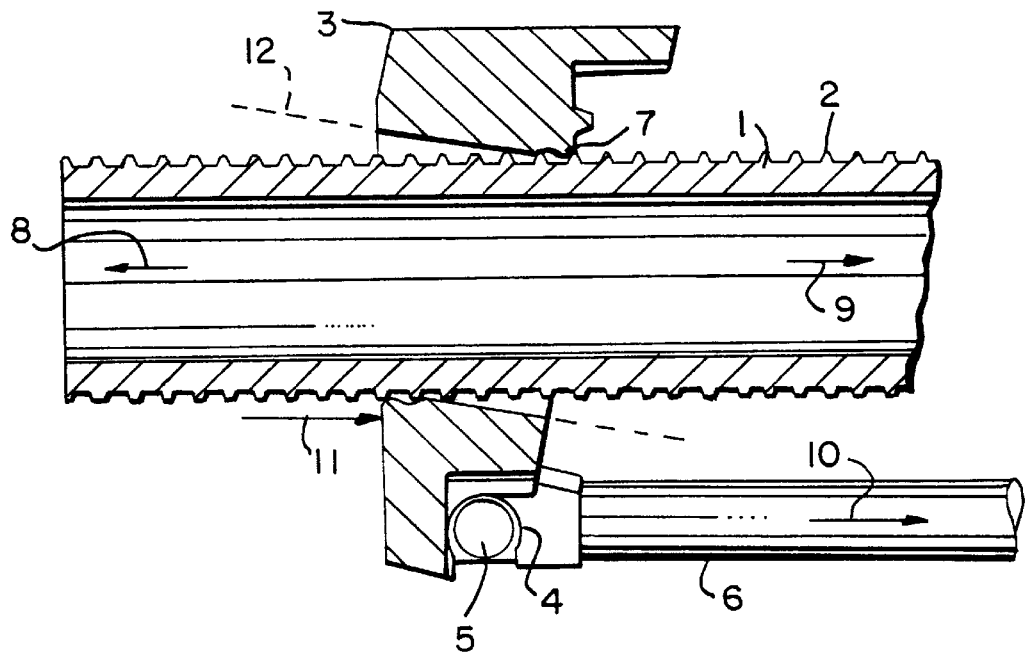

Referring to FIGS. 2 and 5, the a reciprocable and rotatable spindle 1 is provided with an outer thread 2 passing through a nut member 3 which has at a first side a journal 4 in which a pivot pin 5 on a piston rod 6 is journaled. The nut member 3 has two intersecting bores, a first bore coaxial with the spindle 1 in FIG. 1 and a second bore indicated by dotted lines 12 and intersecting the first bore forming an acute angle with this first bore. The first bore has an inner thread 7 which in FIG. 2 engages the outer thread 2 of the spindle 1.

The spindle 1 forms a dose setting member of an injection device in which doses are set by rotating the spindle 1 about its axis. As the nut member is not rotatable, rotation of the spindle 2 will screw this spindle through the nut member 3. A dose is set by screwing the spindle in the direction shown by an arrow 8 and the set dose is injected by moving the spindle 1 without rotating it in the opposite direction shown by an arrow 9. The injection movement of the spindle will due to the engagement of the threads 2 and 7 of the spindle and the nut member, respectively, be transmitted to the nut member 3 and through the journal 4 and the pivot pin 5 further to the piston rod 6 which is moved in the direction indicated by an arrow 10. By the injection movement of the spindle a force is exerted on the nut member 3 as indicated by an arrow 11 which force will try to rotate the nut member 3 about the pivot pin 5 in a direction which brings the threads of the spindle and the nut member in tighter engagement. As shown in FIG. 1, movement of the piston rod 6 in the direction of arrow 10 will push the piston 26 into the cartridge 23, which will expel the set dose.

By successive dose settings and injections the piston rod 6 is moved to its extreme position in the direction indicated by the arrow 10, i.e. the piston 26 upon which the piston rod 6 acts is moved all the way into a cartridge. By the successive dose settings the spindle 1 has been screwed by its full length through the nut member 3 in the direction indicated by the arrow 8. To enable a changing of the cartridge the piston rod 6 has to be withdrawn and the nut member has to be moved from one end of the spindle 1 to the other. To enable such a movement the engagement between the threads of the spindle and the nut member has to be released. This is done by tilting the nut member to a second position so that the smooth walled bore of the nut member becomes coaxial with said spindle as shown in FIG. 3.

Figure 3:
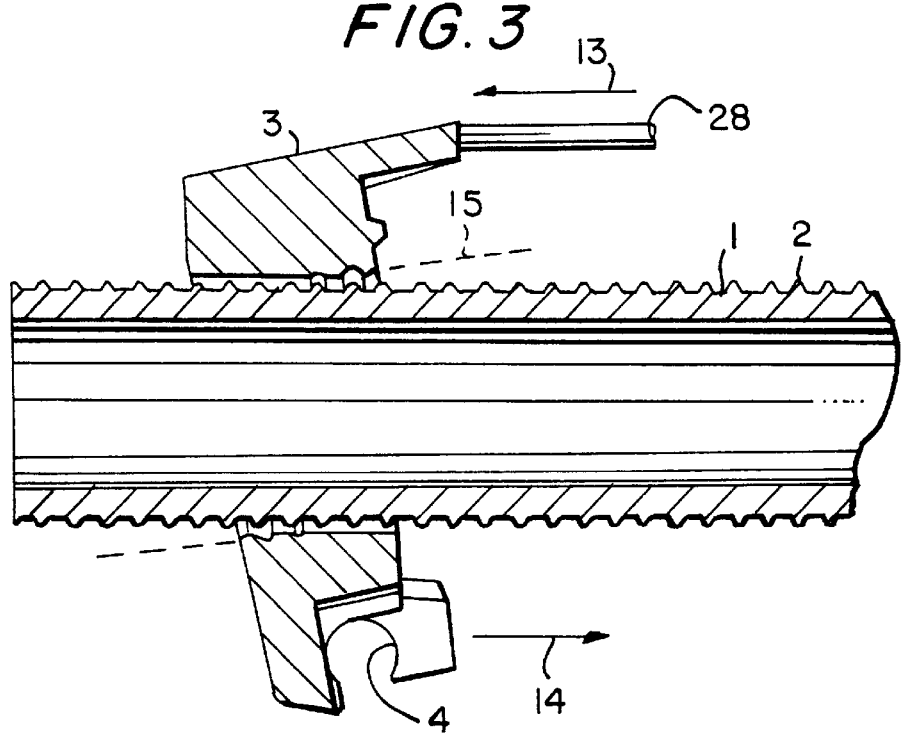

In FIG. 3 the piston rod 6 is omitted. To withdraw the piston rod the nut member must be drawn to the left in the FIG. 3. A drawing force is transmitted to the nut member from a withdrawal element 28 which may be manually operated or automatically operated when a lid is opened to obtain access to an ampoule compartment. The withdrawal element 28 acts by a force indicated by an arrow 13 on a second side of the nut member diametrically opposite said first side. The force indicated by the arrow 13 will together with a force indicated by an arrow 14, originating from the resistance against withdrawal which the piston rod exerts on the nut member, exert a torque on the nut member in a plane defined by the intersecting axis of the bores. This torque will draw the nut member to a second position in which the smooth walled bore is coaxial with the spindle 1 and keep the nut member in this tilted position as long as the withdrawing force is applied. With this second rotational position of the nut member 3 this nut member may be moved along the spindle as the top of the thread 2 of the spindle slides along the smooth wall of the smooth walled bore of the nut member 3. The thread of the nut member is drawn out of engagement with the thread 2 of the spindle 1 as the threaded bore now is positioned as indicated by the dotted lines 15. The nut member can be biased towards its first rotational position in which the threads of the spindle and the nut element are in engagement.

We claim:

1. A syringe comprising a housing including a cartridge holder for receiving a cartridge of the type having a piston, and a dosing mechanism by which a dose may be set and subsequently injected by successively advancing the piston when such a cartridge is mounted in the cartridge holder, said dosing mechanism comprising a spindle having an axis and an outer thread, and a nut member cooperating with the spindle, wherein said spindle and nut member are mounted within said housing so as to be rotatable relative to one another, wherein the nut has a first bore and a second bore which intersect and form an angle with each other, wherein said first bore has an inner thread matching the outer thread of the spindle such that rotation of the spindle relative to the nut member causes the axial position of the nut member relative to the spindle to change, the position of the nut member on the spindle defining how far the piston is advanced during the injection, wherein said second bore is smooth and fits slidingly about the outer thread of said spindle, wherein the nut member is tiltable between a first position, in which the first bore is coaxial with the spindle, and a second position, in which the second bore is coaxial with the spindle, such that said nut member can be moved into its first position during dose setting and injection operations and into its second position when it is desired to move said nut member along the spindle without rotating the spindle, and wherein said syringe further comprises a piston withdrawal member which acts on the nut member at a location such that the nut member is tilted to its second position when a piston rod withdrawal force is applied to said nut member.

2. A syringe comprising a housing including a cartridge holder for receiving a cartridge of the type having a piston, and a dosing mechanism by which a dose may be set and subsequently injected by successively advancing the piston when such a cartridge is mounted in the cartridge holder, said dosing mechanism comprising a spindle having an axis and an outer thread, and a nut member cooperating with the spindle, wherein said spindle and nut member are mounted in said housing so as to be rotatable relative to one another, wherein the nut has a first bore and a second bore which intersect and form an angle with each other, wherein said first bore has an inner thread matching the outer thread of the spindle such that rotation of the spindle relative to the nut member causes the axial position of the nut member relative to the spindle to change, wherein said spindle and said nut member are both axially moveable within said housing, in a direction towards said cartridge holder, to inject a set dose, the position of the nut member on the spindle defining how far the piston is advanced during the injection, wherein said second bore is smooth and fits slidingly about the outer thread of said spindle, and wherein the nut member is tiltable between a first position, in which the first bore is coaxial with the spindle, and a second position, in which the second bore is coaxial with the spindle, such that said nut member can be moved into its first position during dose setting and injection operations and into its second position when it is desired to move said nut member along the spindle without rotating the spindle.

3. A syringe comprising a housing including a cartridge holder for receiving a cartridge of the type having a piston, a piston rod having one end arranged to contact the piston of such a cartridge when the cartridge is mounted in the cartridge holder, and a dosing mechanism by which a dose may be set and subsequently injected by successively advancing said piston rod into such cartridge, said dosing mechanism comprising a spindle having an axis and an outer thread, and a nut member cooperating with the spindle, wherein said spindle and nut member are mounted in said housing so as to be rotatable relative to one another, wherein the nut has a first bore and a second bore which intersect and form an angle with each other, wherein said first bore has an inner thread matching the outer thread of the spindle such that rotation of the spindle relative to the nut member causes the axial position of the nut member relative to the spindle to change, the position of the nut member on the spindle defining how far the piston rod is advanced during the injection, wherein said second bore is smooth and fits slidingly about the outer thread of said spindle, wherein the nut member is tiltable between a first position in which the first bore is coaxial with the spindle, and a second position, in which the second bore is coaxial with the spindle, such that said nut member can be moved into its first position during dose setting and injection operations and into its second position when it is desired to withdraw the piston rod and move said nut member along the spindle without rotating the spindle, and wherein the nut member is hinged to the piston rod at a first location such that exertion of a force by the nut member on the piston rod in a direction by which an injection is performed urges said nut member to tilt into its first position.

4. The syringe according to claim 3, wherein said syringe further comprises a piston withdrawal member which acts on the nut member at a second location such that the nut member is tilted to its second position when a piston rod withdrawal force is applied to said nut member.

5. The syringe according to claim 4, wherein said first and second locations are diametrically opposed.

* * * * *

UNITED STATES PATENT AND TRADEMARK OFFICE
CERTIFICATE OF CORRECTION

| | |
|---|---|
| PATENT NO. | : 5,961,496 |
| DATED | : October 5, 1999 |
| INVENTOR(S) | : Nielsen et al. |

It is certified that error appears in the above-identified patent and that said Letters Patent is hereby corrected as shown below:

<u>Title page, item [60],</u>
Related U.S. Application Data, please delete "Provisional application No. 60/090,993, Jun. 18, 1997", and insert -- Provisional application No. 60/050,993, Jun. 18, 1997 --.

Signed and Sealed this

Sixth Day of November, 2001

Attest:

NICHOLAS P. GODICI
*Attesting Officer*  *Acting Director of the United States Patent and Trademark Office*